United States Patent [19]

Wilk

[11] Patent Number: 5,236,438
[45] Date of Patent: Aug. 17, 1993

[54] METHOD AND ASSEMBLY FOR REPAIRING LIVER LACERATION

[76] Inventor: Peter J. Wilk, 185 West End Ave., New York, N.Y. 10023

[21] Appl. No.: 943,390

[22] Filed: Sep. 10, 1992

[51] Int. Cl.$^5$ .............................................. A61B 17/00
[52] U.S. Cl. .................................... 606/215; 606/216; 411/455
[58] Field of Search ........................... 606/213-216; 411/44, 446, 448, 455, 336

[56] References Cited

U.S. PATENT DOCUMENTS

| | | | |
|---|---|---|---|
| 363,538 | 5/1887 | Penny | 606/216 |
| 1,127,090 | 2/1915 | Reedy | 411/446 |
| 2,199,025 | 4/1940 | Conn | 606/232 |
| 4,711,234 | 12/1987 | Vives et al. | 606/76 |
| 4,757,664 | 7/1988 | Freissle | 411/44 |
| 4,861,208 | 8/1989 | Boundy | 411/339 |

Primary Examiner—Stephen C. Pellegrino
Assistant Examiner—Gary Jackson
Attorney, Agent, or Firm—R. Neil Sudol; Henry D. Coleman

[57] ABSTRACT

In a method for repairing a liver laceration, a plurality of bolts of biocompatible material are provided, each of the bolts being formed with anchoring means for preventing removal of the respective bolt from the liver upon insertion of the bolt therein. At least two of the bolts are driven into the liver on opposite sides of the laceration so that head portions of the two bolts remain protruding from the liver. A suture is tied around the protruding head portions of the two bolts, thereby closing the laceration and stemming a flow of blood from the laceration. The bolts may be provided with molley type sheaths which are pushed into the liver prior to insertion of the two bolts and which are expanded at least in part by the bolts to anchor the sheaths and the bolts in the liver. The sheaths, like the bolts, are made of a biocompatible, even bioabsorbable or hemostatic, material.

22 Claims, 1 Drawing Sheet

METHOD AND ASSEMBLY FOR REPAIRING LIVER LACERATION

BACKGROUND OF THE INVENTION

This invention relates to a method for repairing a liver laceration. More particularly, this invention relates to a method for closing a liver laceration to thereby stem the flow of blood therefrom. This invention also relates to an associated assembly for use in implementing the method.

The liver is a highly vascularized organ and bleeds profusely when lacerated or traumatized. Liver lacerations are difficult and frequently impossible to repair owing to the nature of the liver tissues. Sutures pull through the tissues and come out. Staples are similarly difficult or impossible to use effectively.

Because of the weak cohesiveness of liver tissue and because the veins feeding the liver are difficult or impossible to reach quickly, severe lacerations of the liver commonly result in the patient's bleeding to death.

OBJECTS OF THE INVENTION

An object of the present invention is to provide a method for repairing a lacerated liver.

Another, more particular, object of the present invention is to provide such a method for closing a liver laceration, thereby stemming the flow of blood from the liver.

A further particular object of the present invention is to provide such a method which is relatively easy and quick to implement.

Another object of the present invention is to provide an assembly or surgical prosthesis which may be used to close a liver laceration.

Yet another object of the present invention is to provide such an assembly which may be absorbed by the liver upon healing of a repaired laceration.

These and other objects of the present invention will be apparent from the drawings and detailed descriptions herein.

SUMMARY OF THE INVENTION

A method for repairing a liver laceration comprises the steps of (a) providing a plurality of bolts of biocompatible material, each of the bolts being formed with anchoring means for preventing removal of the respective bolt from the liver upon insertion of the bolt therein, (b) driving two of the bolts into the liver on opposite sides of the laceration so that head portions of the two bolts remain protruding from the liver, and (c) tying a suture around the protruding head portions of the two bolts, thereby closing the laceration and stemming a flow of blood from the laceration.

According to another feature of the present invention, the method further comprises the steps of inserting molley sheaths into the liver, the two bolts being inserted into respective molley sheaths upon insertion thereof into the liver. The bolts expand at least portions of the molley sheaths to anchor the sheaths and the bolts in the liver. The sheaths, like the bolts, are made of a biocompatible material.

An assembly for repairing a liver laceration pursuant to the above-described method comprises, in accordance with the present invention, a plurality of bolts of biocompatible material, each of the bolts being adapted for insertion into the liver. Each of the bolts is provided with anchoring elements for preventing removal of the respective bolt from the liver upon insertion of the bolt therein. In addition, a coupling element such as a suture is provided for tying a protruding portion of one of the bolts on one side of the liver laceration to a protruding portion of another of the bolts on an opposite side of the liver laceration, thereby closing the laceration and stemming a flow of blood from the laceration. An arrest is formed on each of the bolts for preventing the coupling element from slipping off the respective bolts upon tying of the protruding bolt portions to one another.

In accordance with another feature of the present invention, the anchoring elements includes a plurality of expandable molley sheaths made of a biocompatible material, the bolts being inserted into respective ones of the molley sheaths.

According to further features of the present invention, molley sheaths and the bolts are made of a bioabsorbable material with an optional hemostatic coating. Alternatively, the sheaths and the bolts are made of a hemostatic material.

Pursuant to an additional feature of the present invention, the anchoring elements include a plurality of shoulders formed along the shafts of the bolts. In that event, the bolts made be inserted directly into the liver tissues, without intermediate molley sheaths. The shoulders are preferably axially spaced from one another along the bolt shafts.

A method for repairing a lacerated liver in accordance with the present invention reduces fatalities from liver trauma. Liver lacerations are closed quickly and effectively, thereby stemming the flow of blood, with a significantly increased success over conventional suturing or stapling techniques.

DETAILED DESCRIPTION

Figure 1:
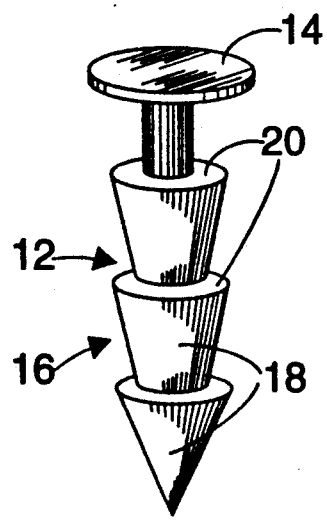
FIG. 1 is a schematic perspective view of a surgical bolt for use in repairing a liver laceration in a method in accordance with the present invention.

As illustrated in FIG. 1, a bolt 12 for use in repairing a liver laceration comprises a head 14 connected to a proximal end of a shaft 16. Shaft 16 is formed with a plurality of conical segments 18 each defining a respective annular shoulder 20. Shoulders 20 are spaced from one another along the length of shaft 16 and serve to anchor bolt 12 in liver tissues upon a pushing or insertion of shaft 16 into the liver tissues.

Figure 2:
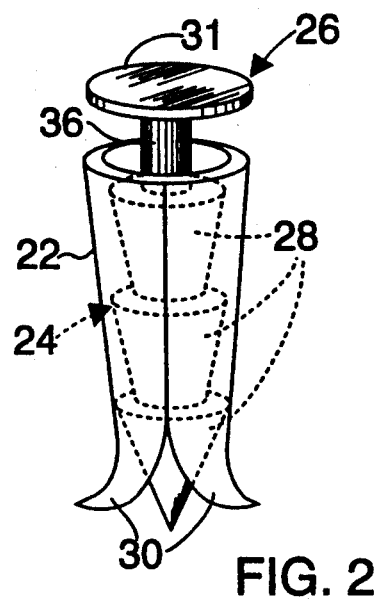
FIG. 2 is a schematic perspective view of a surgical bolt with a molley sheath for use in repairing a liver laceration in a method in accordance with the present invention.

As depicted in FIG. 2, an alternative liver repair tool includes a molley sheath 22 into which a shaft 24 of a bolt 26 is inserted. Bolt 26 has a structure similar or identical to bolt 12 of FIG. 1. Accordingly, shaft 24 of bolt 26 is provided with a plurality of conical segments 28 which serve in part to expand the distal end of sheath 22 to form a plurality of outwardly extending anchor flaps or fingers 30. Flaps or fingers 30 serve to anchor sheath 22 and concomitantly bolt 26 in liver tissues.

Bolt 26 has a flat head 31 connected to shaft 24 at the proximal end thereof.

Figure 3A:
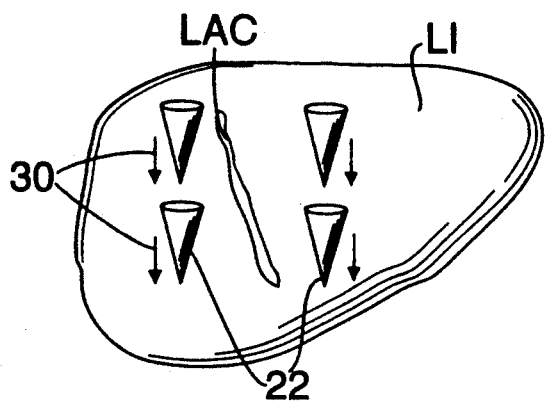
FIGS. 3A–3D are diagrams showing successive stages in a liver laceration repair procedure in accordance with the present invention.
Figure 3B:
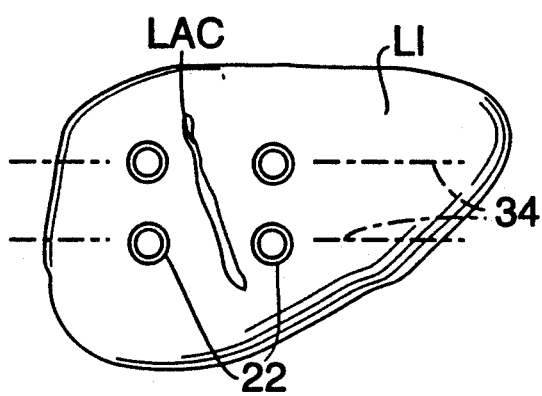

In repairing a liver laceration using the tool of FIG. 2, a plurality of sheaths 22 are pushed or driven into a liver LI along opposite sides of a laceration LAC, as indicated by arrows 32 in FIG. 3A. As shown in FIG. 3B, the sheaths 22 are disposed in pairs along lines 34 oriented substantially perpendicularly to laceration LAC.

Figure 3C:
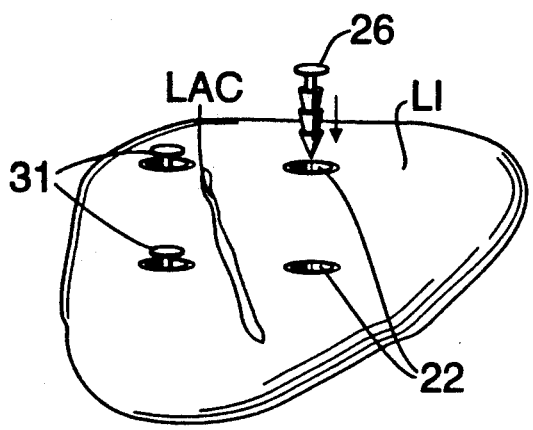
Figure 3D:
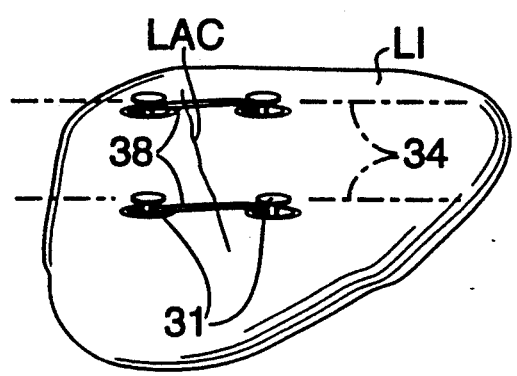

Upon the disposition of sheaths 22 in liver LI, bolts 26 are inserted into the sheaths 22, as depicted in FIG. 3C, so as to form anchoring flaps 30 at the distal or inner ends of the sheaths (see FIG. 2). Bolts 26 are only partially inserted into sheaths 22 so that proximal end or head portions including heads 31 and a shaft neck 36 (FIG. 2) protrude from the surface of liver LI.

Upon the insertion of bolts 26 in sheaths 22, sutures 38 are wrapped around necks 36 of the bolts 26 of aligned pairs, to couple the bolts to one another and thereby close laceration LAC. Upon the tying of sutures 38 about bolt necks 36, the sutures are aligned along lines 34 and effectuate a blood-stopping clamp on the liver.

Instead of molley sheaths 22 and bolts 26, bolts 12 may be used. Bolts 12 are inserted directly into the liver tissues, without the mediation of sheaths 22.

Bolts 12, sheaths 22 and bolts 26, as well as sutures 38, are advantageously made of a bioabsorbable material calculated to dissolve into the liver upon a healing hereof in the eregion of laceration LAC. In addition, a coating of a hemostatic material such as AVATINE TM may be provided on bolts 12 and sheaths 22 and optionally bolts 26, to facilitate blood clotting in the liver tissues upon deployment of the surgical assembly. Alternatively, the bolts and molley sheaths may be made of a hemostatic material.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method for repairing a liver laceration, comprising the steps of:
   providing a plurality of bolts of biocompatible material, each of said bolts being formed with anchoring means for preventing removal of the respective bolt from the liver upon insertion of the bolt therein;
   driving two of said bolts into the liver on opposite sides of the laceration so that head portions of said two of said bolts remain protruding from the liver; and
   attaching a suture around the protruding head portions of said two of said bolts, thereby closing the laceration and stemming a flow of blood from the laceration.

2. The method defined in claim 1, further comprising the steps of inserting molley sheaths into the liver, said two of said bolts being inserted into respective ones of said molley sheaths, thereby expanding at least portions of said molley sheaths to anchor said sheaths and said bolts in the liver, said sheaths being made of a biocompatible material.

3. The method defined in claim 2 wherein said molley sheaths are made of a bioabsorbable material.

4. The method defined in claim 2 wherein said molley sheaths are made of a hemostatic material.

5. The method defined in claim 2 wherein said sheaths are each provided with a coating of a hemostatic agent.

6. The method defined in claim 1 wherein each of said bolts has a shaft and a head at one end of said shaft, said anchoring means including a plurality of shoulders formed along said shaft.

7. The method defined in claim 6 wherein said shoulders are axially spaced from one another along said shaft.

8. The method defined in claim 1 wherein said bolts are made of a bioabsorbable material.

9. The method defined in claim 1 wherein said bolts are made of a hemostatic material.

10. The method defined in claim 1 wherein said bolts are each provided with a coating of a hemostatic agent.

11. A kit for repairing a liver laceration, comprising:
    a plurality of bolts of biocompatible material, each of said bolts being adapted for insertion into the liver;
    anchoring means on each of said bolts for preventing removal of the respective bolt from the liver upon insertion of the bolt therein;
    coupling means for tying a protruding portion of one of said bolts on one side of the liver laceration to a protruding portion of another of said bolts on an opposite side of the liver laceration, thereby closing the laceration and stemming a flow of blood from the laceration; and
    arresting means on each of said bolts for preventing said coupling means from slipping off the respective bolts upon tying of the protruding bolt portions to one another.

12. The kit defined in claim 11 wherein said anchoring means includes a plurality of expandable molley sheaths made of a biocompatible material, said bolts being inserted into respective ones of said molley sheaths.

13. The kit defined in claim 12 wherein said molley sheaths are made of a bioabsorbable material.

14. The kit defined in claim 12 wherein said molley sheaths are made of a hemostatic material.

15. The kit defined in claim 12 wherein said sheaths are each provided with a coating of a hemostatic agent.

16. The kit defined in claim 11 wherein said anchoring means includes a plurality of shoulders formed along a shaft of each of said bolts.

17. The kit defined in claim 16 wherein said shoulders are axially spaced from one another along said shaft.

18. The device defined in claim 11 wherein said coupling means includes a suture.

19. The device defined in claim 11 wherein said arresting means includes a bolt head.

20. The kit defined in claim 11 wherein said bolts are made of a bioabsorbable material.

21. The kit defined in claim 11 wherein said bolts are made of a hemostatic material.

22. The kit defined in claim 11 wherein said bolts are each provided with a coating of a hemostatic agent.

* * * * *